(12) United States Patent
Tan et al.

(10) Patent No.: US 7,732,642 B1
(45) Date of Patent: Jun. 8, 2010

(54) ARYLCARBONYLATED DETONATION NANODIAMONDS

(75) Inventors: Loon-Seng Tan, Centerville, OH (US); David H. Wang, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 12/322,956

(22) Filed: Feb. 5, 2009

Related U.S. Application Data

(60) Provisional application No. 61/070,596, filed on Feb. 21, 2008.

(51) Int. Cl.
C07C 45/00 (2006.01)
C07C 49/303 (2006.01)
(52) U.S. Cl. .................................. 568/319; 568/335
(58) Field of Classification Search ................. 568/319, 568/335
See application file for complete search history.

(56) References Cited

U.S. PATENT DOCUMENTS

| 7,144,753 B2 * | 12/2006 | Swain et al. ................. 438/105 |
| 2005/0158549 A1 * | 7/2005 | Khabashesku et al. ...... 428/403 |
| 2006/0154259 A1 * | 7/2006 | Chang et al. .................. 435/6 |
| 2009/0246887 A1 * | 10/2009 | Chang et al. ................. 436/501 |

FOREIGN PATENT DOCUMENTS

WO    WO2009/038850 A2 *   3/2009

OTHER PUBLICATIONS

Tu et al. Size-dependent surface CO stretching frequency investigations on nanodiamond particles. The Journal of Chemical Physics, 2006, vol. 125, p. 174713-1 to 174713-7.*

* cited by examiner

Primary Examiner—Sikarl A Witherspoon
(74) Attorney, Agent, or Firm—AFMCLO/Jaz; Bart S. Hersko

(57) ABSTRACT

Functionalized detonation nanodiamond particulates of the formula:

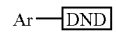

Ar—DND wherein Ar is selected from the group consisting of:

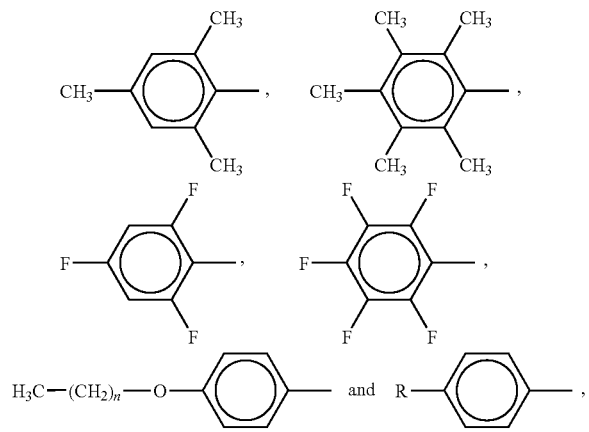

wherein R is selected from the group consisting of H, $H_3C—(CH_2)_n—$ and

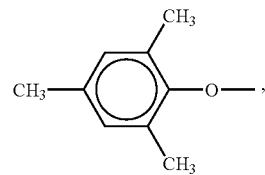

wherein n has a value of 0-10. Also provided is a process for functionalizing detonation nanodiamonds particulates.

2 Claims, No Drawings

ARYLCARBONYLATED DETONATION NANODIAMONDS

CROSS REFERENCE TO RELATED APPLICATION

This application claims priority of the filing date of Provisional Application Ser. No. 61/070,596 filed Feb. 21, 2008.

BACKGROUND OF THE INVENTION

The present invention relates to arylcarbonyl-functionalized detonation nanodiamond (DND) particulates and the method of preparation. In comparison to other members of nanocarbon family, viz. fullerenes, single-walled, double-walled, multi-walled carbon nanotubes (SWNT, DWNT and MWNT) and nanofibers, nanodiamonds (ND) have received much less attention even though they were discovered relatively early (in the 1960's) in USSR. This carbon nanomaterial is known by three popular names: 'ultra-nanocrystalline' diamonds (UNCD) or 'ultra-dispersed' diamond (UDD), because its basic diamond constituents (primary particles) has the characteristic size in the range of 3-6 nm, and detonation nanodiamond (DND, abbreviation used in this disclosure) because of its production by detonation of trinitrotoluene (TNT)/hexogen explosives in a steel chamber. Many of the bulk properties of diamonds are well-understood, but those of nanodiamonds are mostly unexplored. An ab-initio computer simulation studies indicated that a nanodiamond is a structural combination of a diamond core and fullerene-like surface ("bucky diamond"), having both the HOMO and LUMO states localized at the surface and the interface between the diamond core and the fullerenic surface. With the advantages in the availability in larger quantities and at relatively low cost, DND is very attractive as a material platform for nanotechnology. Furthermore, a recent investigation has demonstrated that DND is non-toxic and biocompatible. These features make it attractive for bio-related applications in view of DND's rich surface chemistry that could be modified in a controllable way.

Accordingly, it is an object of the present invention to provide uniquely functionalized detonation nanodiamond particulates with desirable properties.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there are provided functionalized detonation nanodiamonds of the formula:

wherein Ar is selected from the group consisting of:

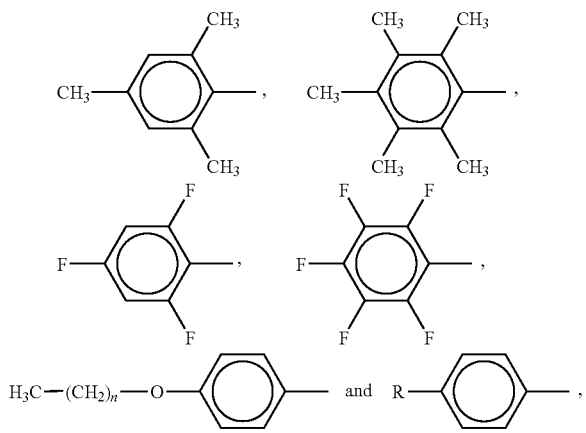

wherein R is selected from the group consisting of H, $H_3C$—$(CH_2)_n$— and

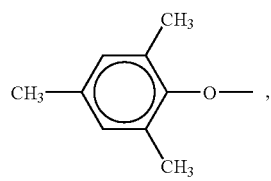

wherein n has a value of 0-10.

DETAILED DESCRIPTION OF THE INVENTION

The functionalized detonation nanodiamonds are prepared in polyphosphoric acid (PPA) at a temperature of about 130° C. An acid Ar—COOH, wherein Ar is as defined above, nanodiamond particles, and PPA (83% assay) are combined and stirred with dried nitrogen purging at about 130° C. for about 3 h. Additional $P_2O_5$ is then added in one portion; and heating is continued, with stirring for about 24-60 hours. The reaction product is then precipitated from the PPA reaction solution with water or other nonsolvent. Suitable aromatic acids useful in this reaction include 2,4,6-trimethylbenzoic acid (mesitylenecarboxylic acid), 1,2,3,4,5-pentamethylbenzoic acid, 2,4,6-trifluorobenzoic acid, 1,2,3,4,5-pentafluorobenzoic acid, 4-alkoxybenzoic acids, benzoic acid, 4-alkylbenzoic acid and 2,4,6-trimethylphenoxybenzoic acid.

Functionalization of the detonation nanodiamond is conducted in polyphosphoric acid (PPA). Preliminarily it is helpful to describe the chemistry of phosphoric acids and strong phosphoric acids or polyphosphoric acids as follows: As used herein the term "phosphoric acid(s)" means commercial phosphoric acid(s) containing 85-86% $H_3PO_4$. The strong phosphoric acids, or polyphosphoric acids referred to as PPA (polyphosphoric acid) are members of a continuous series of amorphous condensed phosphoric acid mixtures given by the formula $$H_{n+2}P_nO_{3n+1}$$

or $$HO-(PO_3H)_n-H$$

where the value of n depends on the molar ratio of water to phosphorus pentoxide present.

In its most general definition, polyphosphoric acid composition can range from distributions where the average value of n is less than unity, giving rise to a mobile liquid, to high values of n, where the polyphosphoric acid is a glass at normal temperatures. Because the species of polyphosphoric acid are in a mobile equilibrium, a given equilibrium composition can be prepared in many ways. For instance, the same distribution or polyphosphoric acid composition could be prepared by either starting with concentrated orthophosphoric acid ($H_3PO_4$, n=1) and driving off water or by starting with phosphorus pentoxide ($P_2O_5$) and adding an appropriate amount of water.

All polyphosphoric acid compositions can be described as a ratio of $P_2O_5$ and water by reducing the various species present (on paper) to $P_2O_5$ and water. We will then use the convention that polyphosphoric acid composition will be expressed in terms of a $P_2O_5$ content (as a percentage) defined as $P_2O_5$ content =(weight of $P_2O_5$)/(weight of $P_2O_5$+weight of water)×100.

Thus, the $P_2O_5$ content of pure orthophosphoric acid could be derived by reducing one mole of $H_3PO_4$ to 0.5 moles $P_2O_5$+ 1.5 moles $H_2O$. Converting to weights gives the $P_2O_5$ content as (0.5*142)/((0.5*142)+(1.5*18.01))*100%=72.4%

Similarly, the $P_2O_5$ content of commercial polyphosphoric acid can be derived in the following way. Polyphosphoric acid is available commercially in two grades, 105% and 115%. These percentages refer to $H_3PO_4$ content, which means that 100 g of the two grades contain 105 and 115 grams of $H_3PO_4$. The $P_2O_5$ content of 115% polyphosphoric acid can then be calculated knowing the $P_2O_5$ content of 100% $H_3PO_4$:

(115 g/100 g)*72.4%=83.3%

The arylcarbonylation reaction, which is a synthetically useful version of Friedel-Crafts reaction, is conducted in polyphosphoric acid (PPA) at a polymer concentration of about 5 weight percent at a temperature of about 130° C. The acid, detonation nanodiamond (DND), and PPA (83% assay) are combined and stirred with dried nitrogen purging at about 130° C. for about 3 hours. Additional $P_2O_5$ is then added in one portion; and heating is continued, with stirring for about 24-60 hours. The reaction product is then precipitated from the PPA reaction solution with water or other polymer nonsolvent. The amount of $P_2O_5$ added is optimized at 25 wt % of the PPA used at the beginning of the reaction, leading to a total $P_2O_5$ content of about 86.7%.

The following examples illustrate the invention:

Example 1

4-(2,4,6-Trimethylphenoxy)benzonitrile

Into a 250 mL three-necked, round-bottomed flask equipped with a magnetic stir-bar, nitrogen inlet, and a condenser, 2,4,6-trimethylphenol (6.00 g, 44.1 mmol), 4-fluorobenzonitrile (5.34 g, 44.1 mmol), potassium carbonate (7.30 g, 52.8 mmol), and a mixture of NMP (100 mL) and toluene (60 mL) were placed. The reaction mixture was then heated and maintained around 140° C. for 8 h with vigorous nitrogen flow. The dark solution was filtered while it was warm and the filtrate was poured into distilled water containing 5% hydrochloric acid. The solution was separated into organic layer and aqueous layer. The organic layer was diluted with dichloromethane and separated. The solvent was removed to dryness. Light brown oily residue was freeze-dried to afford 10.1 g (97% yield): Anal. Calcd. for $C_{16}H_{15}NO$: C, 80.98%; H, 6.37%; N, 5.90%; O, 6.74%. Found: C, 80.31%; H, 6.37%; N, 5.75%; O, 6.46%. FT-IR (KBr, cm$^{-1}$): 2226 (C≡N stretch). Mass spectrum (m/e): 237 (M$^+$, 100% relative abundance), 222, 204, 194. $^1$H NMR (CDCl$_3$, ppm) δ 2.05 (s, 6H, CH$_3$), 2.30 (s, 3H, CH$_3$), 6.81-6.84 (d, 2H, Ar), 6.91 (s, 2H, Ar), 7.53-7.56 (d, 2H, Ar). $^{13}$C NMR (CDCl$_3$, ppm) δ 16.10, 20.79, 115.48, 129.07, 129.15, 129.88, 130.48, 134.25, 147.84, 150.03, 161.44.

Example 2

4-(2,4,6-Trimethylphenoxy)benzoic acid

Into a 250 mL three-necked round-bottomed flask equipped with a magnetic stir-bar, nitrogen inlet, and a condenser, 4-(2,4,6-trimethylphenoxy) benzonitrile (10.0 g, 42.0 mmol) and phosphoric acid (100 mL) were placed. The reaction mixture was then heated and maintained around 150° C. for 8 h. After cooling down to room temperature, the mixture was poured into distilled water containing 5% hydrochloric acid. The resulting precipitates were collected by suction filtration, air-dried, dissolved in warm heptane, and filtered. The filtrate was allowed to cool to room temperature to afford 4.5 g (42% yield) of white crystal: mp 236-238° C. Anal. Calcd. for $C_{16}H_{16}O_3$: C, 74.98%; H, 6.29%; O, 18.73%. Found: C, 74.76%; H, 6.67%; O, 18.56%. FT-IR (KBr, cm$^{-1}$): 1650 (C═O stretch), 3385 (O—H stretch). Mass spectrum (m/e): 256 (M$^+$, 100% relative abundance), 255. $^1$H NMR (DMSO-d$_6$, ppm) δ 2.00 (s, 6H, CH$_3$), 2.67 (s, 3H, CH$_3$), 6.74-6.77 (d, 2H, Ar), 6.98 (s, 2H, Ar), 7.82-7.86 (d, 2H, Ar). $^{13}$C NMR (DMSO-d$_6$, ppm) δ 15.80, 20.41, 113.80, 127.65, 129.69, 129.81, 130.12, 134.47, 147.95, 159.95, 167.06.

Example 3

Functionalization of DND with 4-(2,4,6-trimethylphenoxy)benzoic acid (TMPB-g-DND)

Into a 100 ml resin flask equipped with a high torque mechanical stirrer, and adaptors for nitrogen inlet and outlet, TMPBA (0.20 g, 0.78 mmol), DND (0.20 g), PPA (83% $P_2O_5$ assay, 10 g) and phosphorus pentoxide ($P_2O_5$, 2.5 g) were charged, and the reaction mixture was stirred under dried nitrogen purging at 130° C. for 72 h. After cooling down to room temperature, water was added to the reaction mixture. The resulting precipitate was collected, washed with diluted ammonium hydroxide and Soxhlet extracted with water for three days and methanol for three days. It was then dried over $P_2O_5$ under reduced pressure at 100° C. for 72 h to afford 0.31 g (80% yield) of gray solid. Anal. Calcd. for $C_{7.89}H_3N_{1.75}O_{0.56}$ (based on the assumption that for every 100 carbon, there are 2.35 4-(2,4,6-trimethylphenoxy)benzoyl groups attached): C, 87.58%; H, 2.10%; N, 1.75%; O, 7.01%. Found: C, 86.73%; H, 1.58%; N, 1.90%; O, 7.51%. $^1$H-NMR (DMSO-d$_6$, δ in ppm): 2.03 (s, 6H), 2.27 (s, 3H), 6.88 (d, 2H), 7.001 (s, 2H), 7.69 (d, 2H). FT-IR (KBr, cm$^{-1}$): 3418 (OH), 2922 (CH$_3$), 1712 (O—C═O), 1658 (C═O), 1595, 1234, 1157, 1079.

Having thus described exemplary embodiments of the present invention, it should be noted by those skilled in the art that the disclosures herein are exemplary only and that alternatives, adaptations and modifications may be made within the scope of the present invention.

We claim:
1. Functionalized detonation nanodiamonds particulates of the formula:

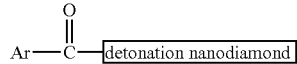

wherein Ar is selected from the group consisting of:

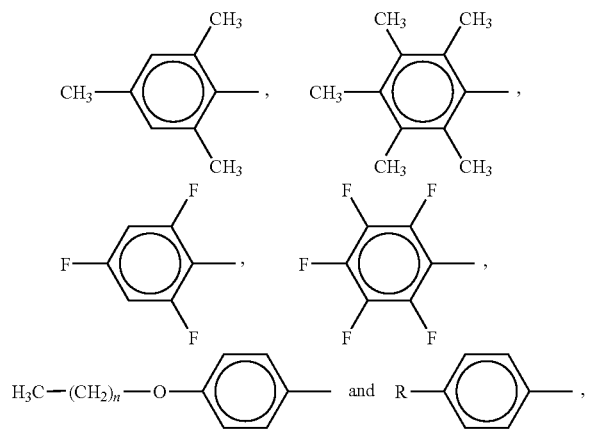

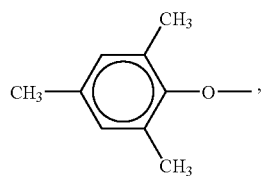

wherein n has a value of 0-10.

2. A process for preparing functionalized detonation nanodiamonds particulates of the formula:

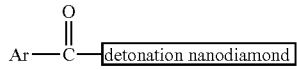

wherein Ar is selected from the group consisting of:

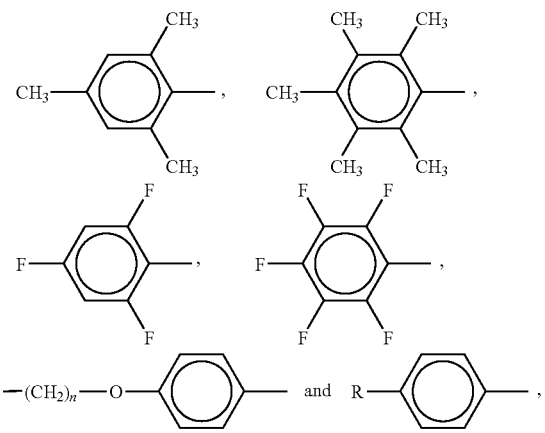

wherein R is selected from the group consisting of H, $H_3C-(CH_2)_n-$ and

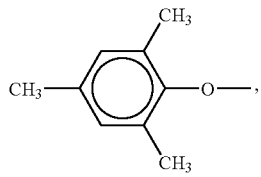

wherein n has a value of 0-10, which comprises the steps of (a) combining an acid Ar—COOH, wherein Ar is as defined above, detonation nanodiamonds particulates, and 83% PPA, (b) stirring this mixture at about 130° C. for about 3 hours, (c) adding additional $P_2O_5$, (d) continuing to heat the mixture with stirring for about 24-60 hours, and (e) recovering the reaction product.

* * * * *